United States Patent [19]
Brekke et al.

[11] 4,151,843
[45] May 1, 1979

[54] APPARATUS FOR ADMINISTRATION OF A GAS TO A HUMAN AND THE EXHAUSTING THEREOF

[76] Inventors: John H. Brekke, 214 5th. Ave., Duluth, Minn. 55792; Devin R. Lacke, 6927 Stevens Ave., Richfield, Minn. 55423

[21] Appl. No.: 851,471

[22] Filed: Nov. 14, 1977

Related U.S. Application Data

[63] Continuation of Ser. No. 700,083, Jun. 28, 1976, abandoned.

[51] Int. Cl.$^2$ ............................................. A61M 16/00
[52] U.S. Cl. .................................... 128/203; 128/206; 128/145.8
[58] Field of Search ............... 128/203, 205, 206, 208, 128/195, 198, 201, 140 R, 140 N, 141 R, 142 R, 142.3, 145.8, 145.7, 145.6, 147

[56] References Cited

U.S. PATENT DOCUMENTS

| | | | |
|---|---|---|---|
| 2,208,633 | 7/1940 | Heidbrink | 128/188 X |
| 2,259,817 | 10/1941 | Hawkins | 128/206 |
| 2,663,297 | 12/1953 | Turnberg | 128/206 |
| 2,820,651 | 1/1958 | Phillips | 128/206 X |
| 3,046,989 | 7/1962 | Hill | 128/206 |
| 3,292,623 | 12/1966 | Warren | 128/203 |
| 3,389,698 | 6/1968 | Kadosch et al. | 128/203 |
| 3,682,171 | 8/1972 | Dali et al. | 128/206 |
| 3,799,164 | 3/1974 | Rollins | 128/206 |
| 3,800,793 | 4/1974 | Marrese et al. | 128/188 |
| 4,015,598 | 4/1977 | Brown | 128/206 |

FOREIGN PATENT DOCUMENTS

| | | | |
|---|---|---|---|
| 2213764 | 9/1973 | Fed. Rep. of Germany | 128/188 |
| 27600 of | 1903 | United Kingdom | 128/206 |

*Primary Examiner*—Henry J. Recla
*Attorney, Agent, or Firm*—Wicks & Nemer

[57] ABSTRACT

An apparatus for administration of a gas to a human and the exhausting thereof including a gas flow control connected to one end of a gas administering device which has on the other end protrusions for sealing engagement with nostrils of the nose. A gas supply conduit is connected to the gas flow control and a gas exhaust conduit is connected to the gas flow control, the gas flow control causes an intake of gas through the supply conduit and said gas administering device and out said protrusions thereon upon inhalation of a user of the apparatus. The gas flow control causes the exhausting of exhaust gas from said gas administering device through said gas flow control and out said gas exhaust conduit to a gas collector upon expiration of the user of the apparatus.

The gas flow control causes the flow of fresh gas through a supply conduit to be blocked during user expiration.

4 Claims, 14 Drawing Figures

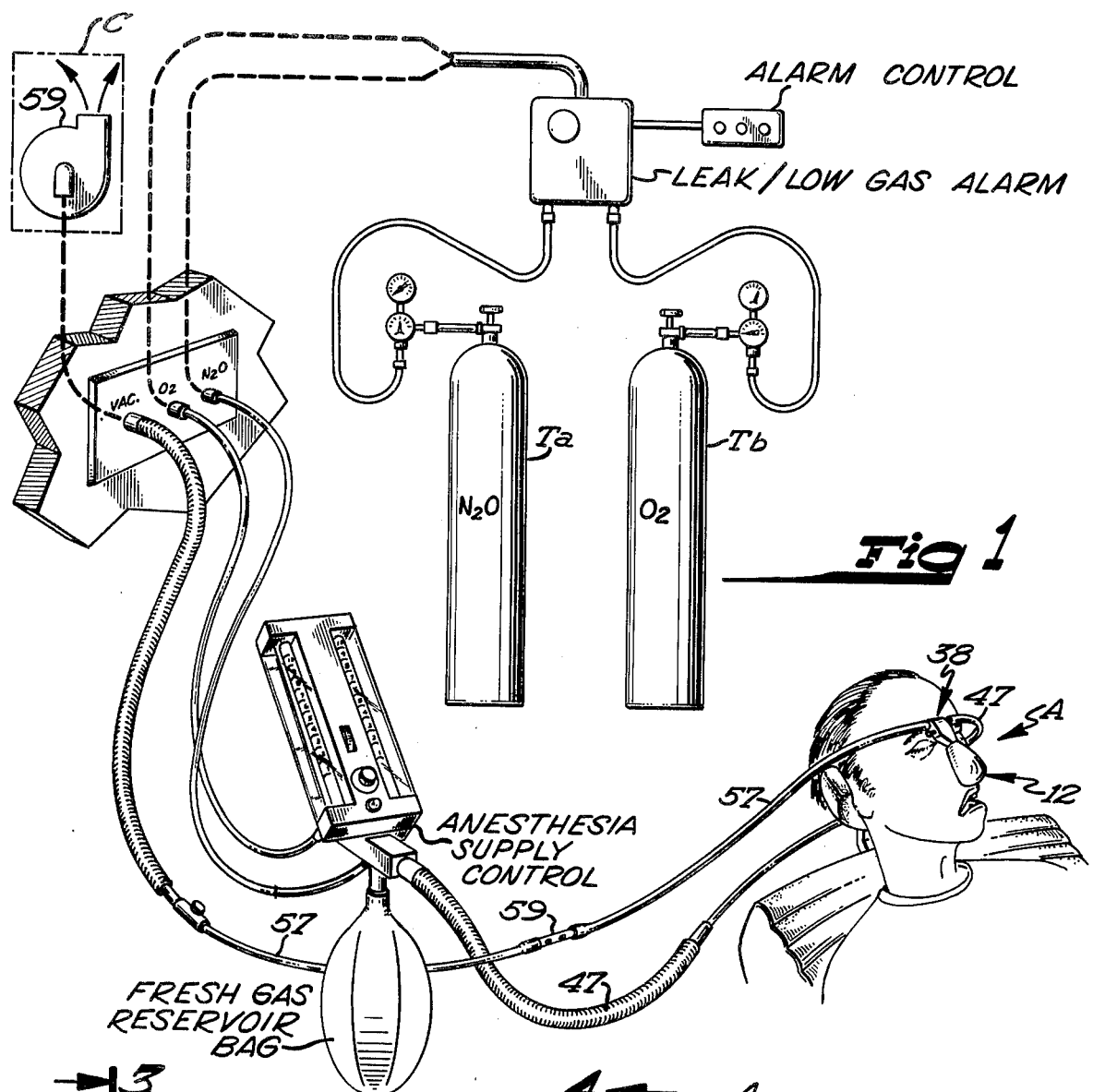
*Fig 1*
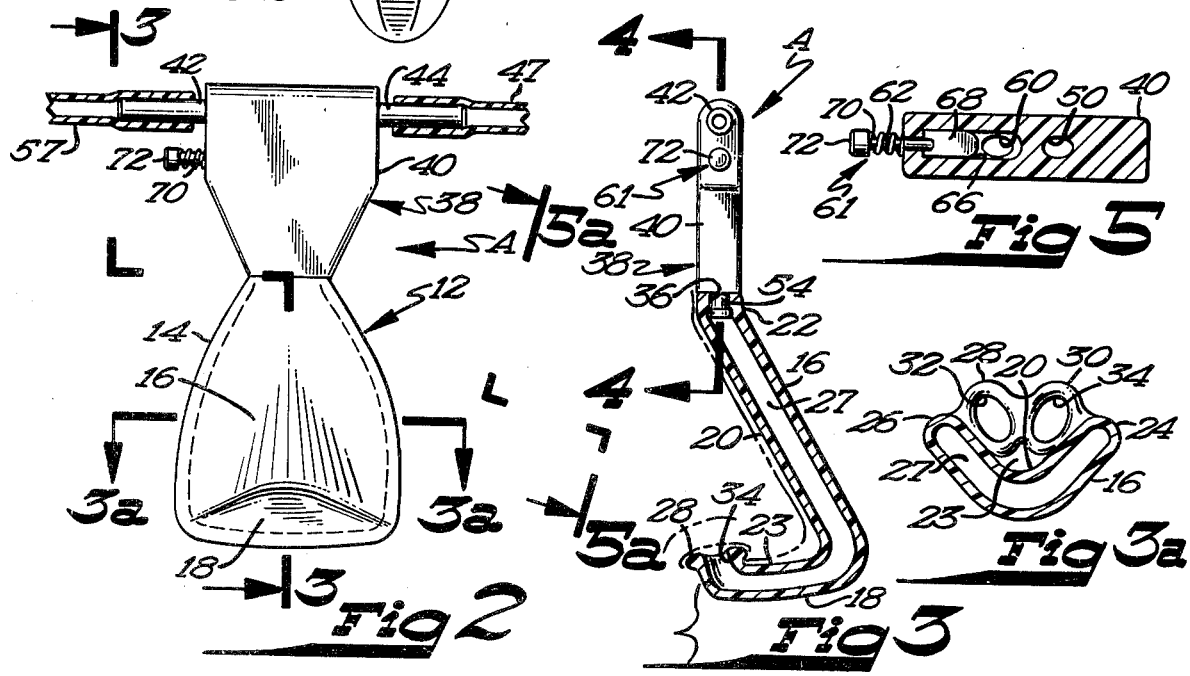

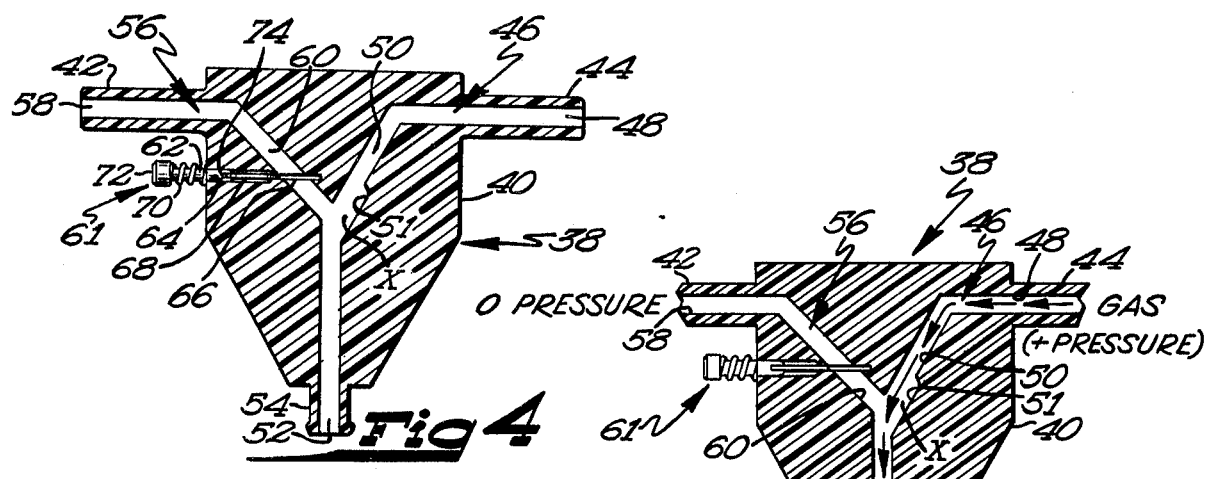
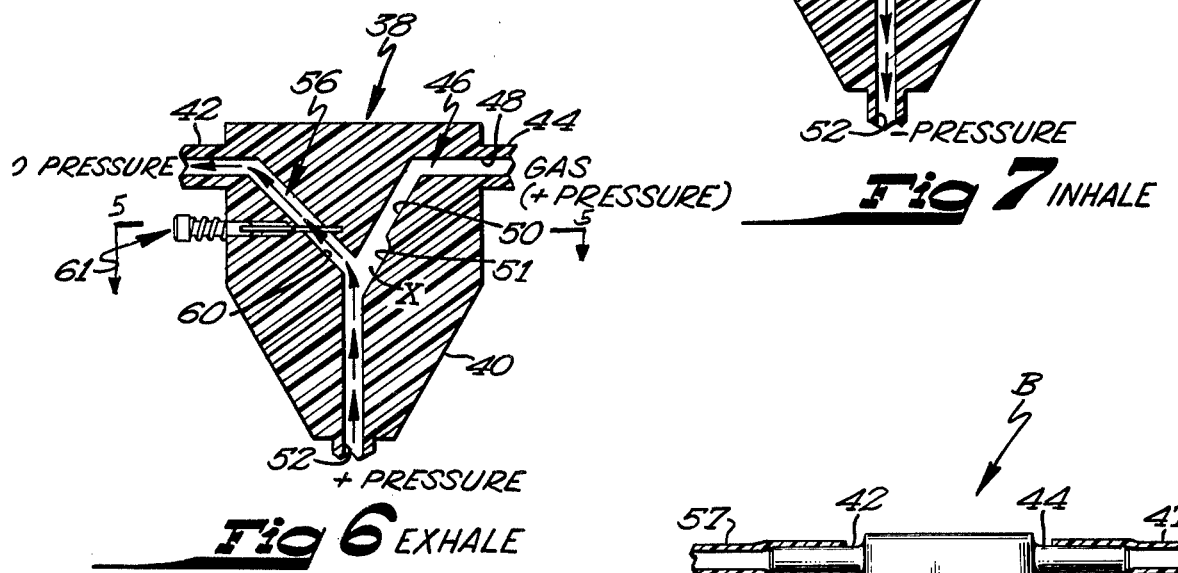
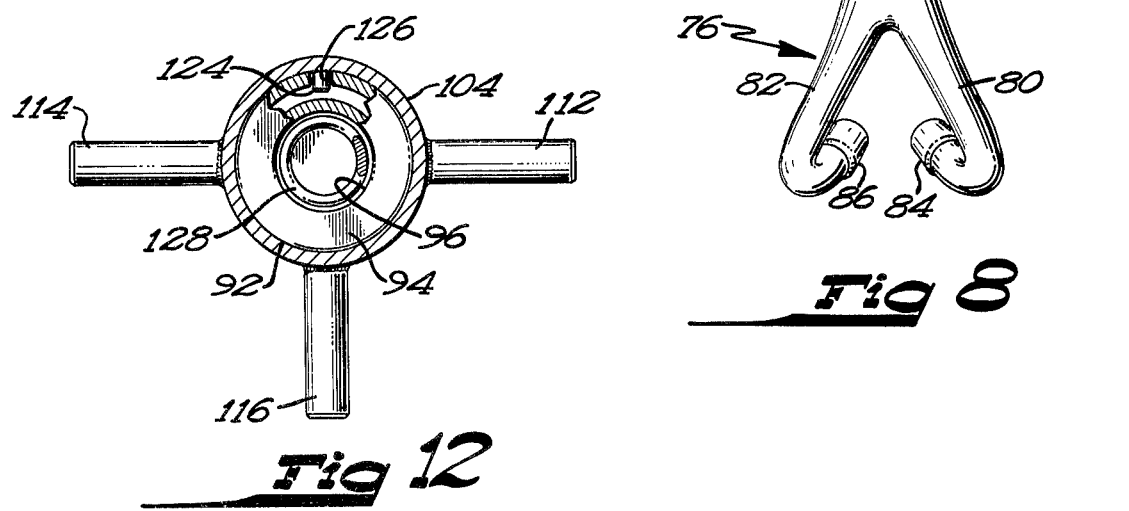

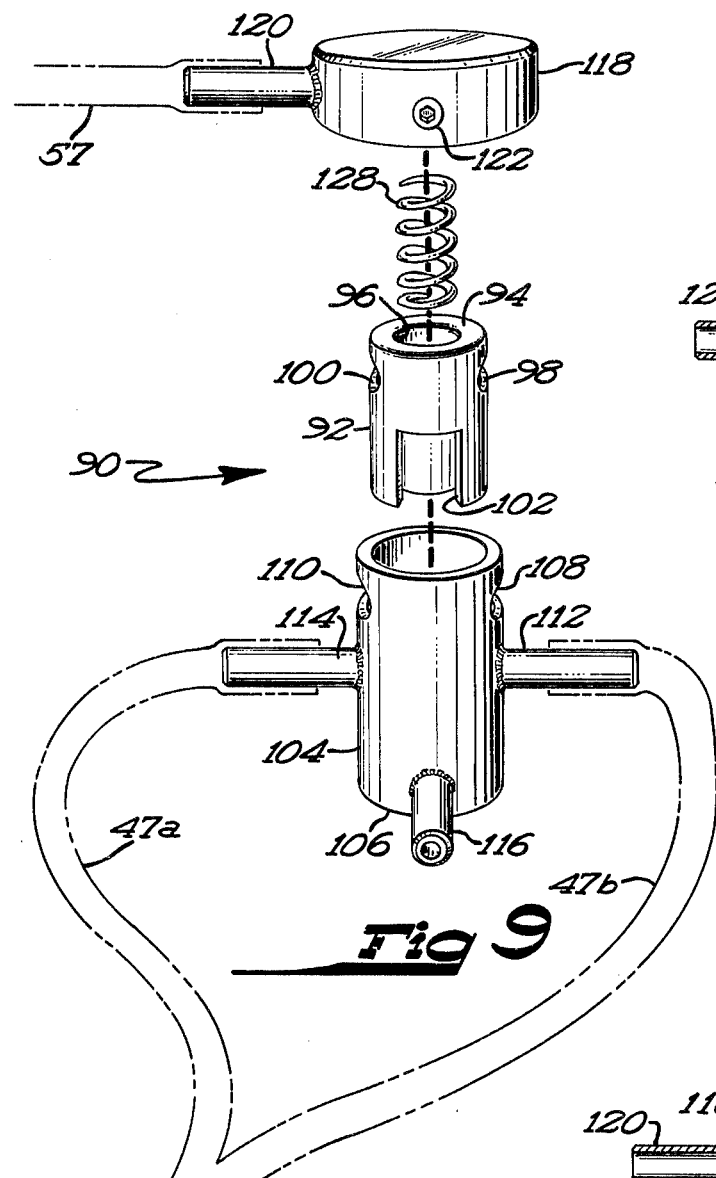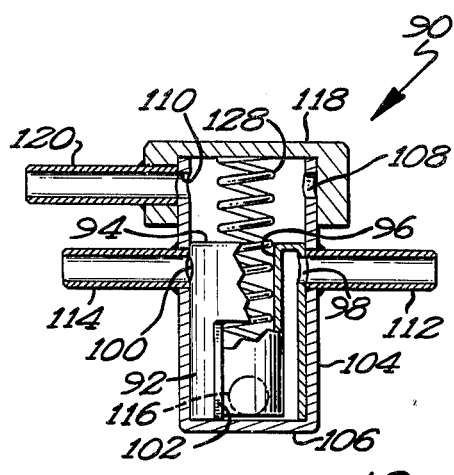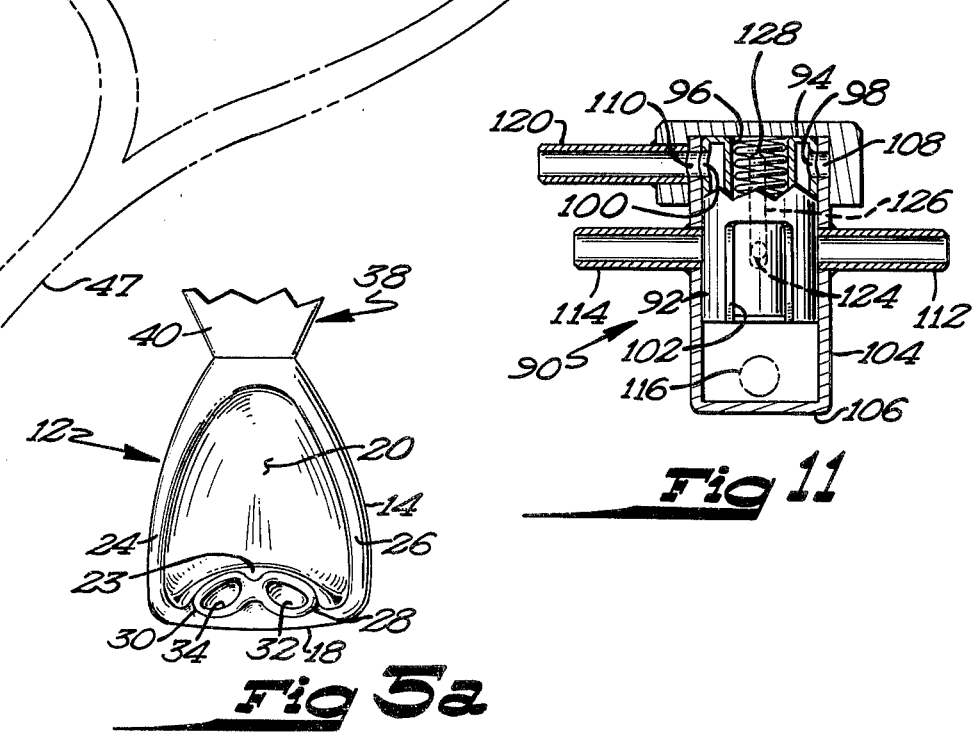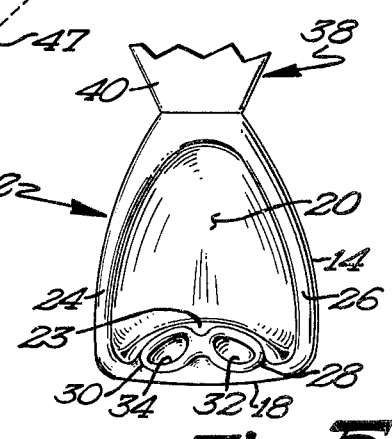

APPARATUS FOR ADMINISTRATION OF A GAS TO A HUMAN AND THE EXHAUSTING THEREOF

CROSS REFERENCE

This is a continuation of application Ser. No. 700,083 filed June 28, 1976, and now abandoned.

SUMMARY

The invention relates to improved devices for the administration of inhalation anesthesia and oxygen to patients requiring out-patient surgical as well as dental procedures. The conventional nasal hood presently used for the administration of inhalation anesthetics and oxygen on an out-patient or ambulatory basis has several disadvantages. These disadvantages include interference with access to the surgical fields of the anterior maxilla, allowing leakage of fresh anesthetic gases and oxygen into the surgical operatory thus wasting expensive anesthetic gases and producing a health hazard in the form of gaseous pollutants inhaled by those performing and assisting in anesthesia and surgery. The conventional nasal hood also allows for inspiration of atmospheric air around its borders which dilutes the anesthetic gases that are inhaled thus reducing their effectiveness. Additionally, the conventional hood fails to provide for safe collection and disposal of anesthetic and patient exhaust gases.

The device herein described is composed of two component parts. The first part is an anesthetic gas flow control which functions during inspiration to direct the flow of fresh anesthetic gases and oxygen into the patient and conducts, upon expiration, the flow of patient exhaust gases into a vacuum scavenging device while simultaneously shutting off the flow of fresh gases to the patient. The second component part is a nasal administration device which attaches to the anesthetic gas flow control. The nasal administration device is presented in two different design forms both of which have the same functions. One form includes a mask attached to the gas flow control and the other form includes a pair of nasal cannulas attached to the gas flow control.

The mask is hollow and covers the entire nose and terminates in two projections on its inner surface which engage the external portions of the nasal orifices bilaterally thereby preventing leakage of gases out of or into the system at that point. The anesthetic and exhaust gases pass from the flow control to the nose and vice versa through the hollow space in the mask.

In the second form the intranasal cannula has two tubes each of which has a compressible cuff on the nostril end which assures a positive seal between the patient's nostril and the tube which prevents leakage of fresh and waste gases into the surgery environment. It also prevents inspiration of atmospheric air through leaks in the system which, if allowed, dilutes the anesthetic gases and the desired amounts of pure oxygen.

With the devices of the invention hereinafter presented there is a closed circuit of gas flow to the patient and from the patient to a scavenging device whereby there is no escape of gas into the operatory which is a health hazard and found in connection with the use of conventional nasal hoods. Further there is a saving of expensive anesthesia gases. Additionally, with the devices disclosed there is free access to the surgical fields whereas with conventional nasal hoods access is restrictive.

In the drawings forming part of this application:

FIG. 1 is a perspective and diagrammatic view of an inhalation anesthetic administration and waste gas scavenging device showing one embodiment of the invention (double walled nasal mask) and illustrated in operative position on a patient. The device is shown hooked up to a conventional gas supply and control apparatus.

FIG. 2 is a front elevational view of a anesthesia gas flow control with nasal mask.

FIG. 3 is a sectional view on the line of 3—3 of FIG. 2.

FIG. 3a is a sectional view on the line of 3a—3a of FIG. 2.

FIG. 4 is a sectional view on the line 4—4 of FIG. 3.

FIG. 5 is a sectional view on the line 5—5 of FIG. 4.

FIG. 5a is a view on the line 5a—5a of FIG. 3.

FIG. 6 is a view similar to FIG. 4, but with the exhale gas flow shown.

FIG. 7 is a view similar to FIG. 6, but with the inhale gas flow shown.

FIG. 8 is a front elevational view of a further embodiment of the invention with the anesthesia gas flow control and intranasal cannula.

FIG. 9 is an exploded perspective of a further embodiment of a gas control device.

FIG. 10 is a longitudinal sectional view of the control of FIG. 9 in assembled and inhale condition.

FIG. 11 is a view similar to FIG. 10 but with the device in exhale condition.

FIG. 12 is a transverse sectional view through the piston and cylinder of the control of FIGS. 9-11.

Referring to the drawings in detail, the device A includes a gas administering device in the form of the double walled hollow mask member 12 which includes the generally pear shaped body 14 formed of the curved front wall 16 terminating in the lower bottom wall 18. Further provided is the curved inner wall 20 joined at its upper end to the top portion 22 and terminating at its lower end in the upper bottom wall 23. The upper end of the front wall 16 also terminates in the top portion 22. The walls 16 and 20 are joined at the side edges by the sidewalls 24 and 26 thereby forming a mask 12 having the hollow interior 27. Extending upwardly from the lower walls 18 and 23 are the spaced protrusions 28 and 30 formed with the openings 32 and 34, respectively, both of which communicate with the hollow interior 27.

The hollow interior 27 terminates at its upper end in the opening 36, formed in the top portion 22. The nostril cuffs 28 and 30 are of a length to extend slightly into the nostrils of a patient receiving anesthesia to form a sealing engagement therewith, and the front wall is of such a lateral extent that the sidewalls 24 and 26 lie adjacent the side of the nose.

The numeral 38 designates a anesthesia gas flow control which includes the body 40. The body 40 is formed with the opposed extensions 42 and 44 on the sides thereof for connection with tubular lines hereinafter referred to. The body 40 is formed with the intake conduit 46 which includes conduit 48 and conduit 50 and recess 51. Extension 44 mounts the anesthesia and oxygen supply line 47. The conduit 48 is obliquely disposed to the intake conduit portion 50 which in turn terminates in the central conduit portion 52.

The conduit portion 50 is formed with the recess 51 adjacent the end thereof and the conduit portion 52 terminates at the extension 54 formed on the lower end of the body 40. the extension 54 is frictionally received in the opening 36 of the mask 12 thereby mounting the control device 38 on the mask.

The body 40 is also formed with the exhaust conduit 56 which includes the conduit portion 58 terminating in the obliquely disposed conduit portion 60 which intersects with the junction of conduit 50 with conduit portion 52 and at the recess 51. Further provided is the exhaust block valve 61 including the shaft 62 mounted in the hole 64 formed in the body 40 and terminating in the slot 66 which slot intersects the conduit portion 60. The shaft has on the inner end thereof the paddle 68 and mounted on the shaft 62 is the coil spring 70 between the head 72 of the shaft and the side of the body 40 thereby normally urging the paddle portion 68 out of the conduit 58. The block valve 61 is prevented from moving out of the body 40 by means of the paddle portion 68 contacting the shoulder 74 formed by the juncture of slot 66 and hole 64. The valve 61 is used for blocking the exhaust conduit consisting of conduits 58 and 60. The block valve 61 mechanically blocks the exhaust side of the control device so that anesthetic gases and oxygen or just oxygen can be forced under pressure through the control device into the patient when necessary without losing any gas out conduit 58.

The flow control 38 is fluidic in nature and when the patient inhales as in FIG. 7, gas under low pressure enters control device body 40 through line 47 and travels through intake conduit 46 and central conduit 52 and into the hollow mask 12, out through the openings 32 and 34 of the protrusions 28 and 30, respectively, and into the nose of the patient. This flow of gas does not flow through exhaust conduit 56 on inspiration because of a "wall attachment" phenomenon which is aided by recess 51. On the other hand when the patient exhales, as shown in FIG. 6, exhaust gas pressure created in central conduit 52 exits out conduit portion 60 of exhaust conduit 56 which is at ambient pressure and into exhaust line 57 in which there is a conventional vacuum interface 59. Exhaust gases collected at the vacuum interface 59 are routed into container C, whereby no exhaust gases enter the room in which the patient is treated. Also the exhaust gas pressure is great enough to overcome the fresh gases at point X, which is the juncture of conduits 50, 52, and 60, thereby blocking the flow of the fresh gases from conduit 46 while the patient is exhaling. With the blocking of the fresh gases the same cannot enter either conduit 50 or conduit 48 which form the intake conduit 46. With the mask 12 fitting against the face adjacent the sides of the nose and the cuffs 28 and 30 snugly fitting against the patient's nostrils, there is no escape of gas into the operatory room, but the gas is scavenged to a point remote from the operatory.

In FIG. 8 is illustrated a further embodiment B of the invention which includes the gas flow control device 38 hereinbefore described. Further included is a gas administering device in the form of the intranasal cannula member 76 which includes the base portion 78 from which emanates the cannula tubes 80 and 82. The base 78 is formed with a socket which frictionally receives the extension 54 for attachment of the cannula 76 to the control device 38. The outer ends of the tubes 80 and 82 are formed with the enlarged nose cuff ends 84 and 86, respectively. The device of FIG. 8 is used by the oral and maxillofacial surgeon when the patient is anesthetized in the surgical planes of anesthesia. This is contrasted with use of the double wall, hollow nasal mask 12 for maintenance of inhalation sedation or amnesic planes of anesthesia.

In FIG. 9 the gas flow control 90 includes the hollow piston 92 having the head 94 in which is formed the socket 96. Formed in the wall of the piston is the first port 98 and an opposed second port 100 together with the cutout 102. The numeral 104 designates a cylinder closed by the bottom wall 106 and formed with the opposed first and second ports 108 and a second intake conduit 114 in line with port 110. Formed on the lower end of the cylinder is the hollow extension 116 which is connected to the cannula 76 or the mask 12.

The numeral 118 designates a cap having the exhaust conduit 120 which attaches to exhaust line 57. Further provided is the thumb screw 122 on the wall of the cap 118. The cylinder has formed on the inner surface of the wall the projection 124 which is positioned in the slot 126 formed in the wall of the piston 92 thereby preventing rotational movement of the piston in the cylinder. The control 90 is assembled by inserting the piston in the cylinder and securing the cap on the cylinder with the coil spring 128 in the recess 96 and against the cap 118. The cap is then secured on the cylinder by means of the thumb screw 122.

In FIG. 10 the control is in the inhalation position with gas flowing in through conduits 112 and 114 and through ports 98 and 100 and down and out through hollow extension 116 connected to the cannula 76 or mask 12. Upon exhalation as in FIG. 11 the piston 92 is moved against the spring due to exhaling pressure, and as a result conduits 112 and 114 are blocked off thereby conserving fresh gases and port 100 aligns with exhaust conduit 120 which is connected to a source of scavenging vacuum. It will be seen that the flow control 90 can be used in lieu of the control 38 with supply line 47 branching off into branch lines 47a and 47b as in FIG. 9.

It will be seen that with the protrusions 28 and 30 of the mask 12 or with the cuffs 84 and 86 of the cannula 76 in sealing contact with the nostrils of a patient we have a closed circuit from the supply tanks Ta and Tb to the point of collection at container C. With the structure disclosed there is a closed system with no escape of gas into the operatory. Further it will also be seen that with either the cannulas or mask in operative position that there is free access to the surgical fields of the oral cavity which is not the case with conventional nasal hoods.

It will also be seen that with the control 38 or 90 fresh gases are automatically blocked during expiration under routine operating conditions.

Having thus described the invention, what is claimed as new and desired to be secured by Letters Patent is:

1. A gas flow control for use in combination with a gas administering device, said flow control comprising:
   (a) a fixed body,
   (b) said body member having an intake conduit terminating in,
   (c) a single exhaust conduit separate from said intake conduit and joining said intake conduit in V-formation,
   (d) a central conduit formed in said body and intersecting the apex of the V-formation of said intake conduit and said single exhaust conduit,
   (e) means for attaching a gas supply line to said intake conduit, and
   (f) means for attaching an exhaust gas line to said exhaust conduit, (g) gas administering means connected to said central conduit whereby during inspiration by a user the flow of intake fresh gas is through said intake conduit and said central conduit in one direction and upon expiration patient exhaust gases flow through said central conduit in the opposite direction and out through said single exhaust conduit, (h) said exhaust conduit having manually operable means located therein for occluding the flow of fresh intake gases therethrough whereby the flow of fresh intake gases through said intake conduit are blocked from entering said exhaust conduit and directed to enter said central conduit at said V-formation to allow forced inspiration of fresh intake gases through said intake conduit.

2. An apparatus for administration of a gas to a human and the exhausting thereof comprising in combination:
  (a) a gas flow control including a fixed body member,
  (b) said body member having an intake conduit portion terminating in,
  (c) a single exhaust conduit separate from said intake conduit formed in said body and joining said intake conduit in a V-formation.
  (d) a central conduit formed in said body and intersecting said intake and exhaust conduits at the apex of the V-formation of said intake conduit and said single exhaust conduit,
  (e) a gas administering device including a base portion having,
  (f) an opening,
  (g) a pair of intranasal cannulas extending from said base portion and communicating with said opening,
  (h) means connecting said base portion of said gas administering device directly with said central conduit of said gas flow control with said opening of said gas administering device directly communicating with said central conduit,
  (i) said cannulas having means on the outer free ends thereof for sealing engagement with the nostrils of a human nose, and
  (j) gas collector means connected to said single exhaust conduit,
  (k) the flow of exhaust gas from the nose of a patient through said central conduit and said single exhaust conduit blocking the flow of intake gas through said gas flow control and allowing the exhausting of exhaust gas solely from said exhaust conduit of said gas flow control to exhaust gas collector means located in an area separated from the apparatus, and
  (l) means for connecting said intake conduit to a supply of gas,
  (m) said exhaust conduit having manually operable means located therein for occluding the flow of fresh intake gases therethrough whereby the flow of fresh intake gases through said intake conduit are blocked from entering said exhaust conduit and directed to enter said central conduit at said V-formation to allow forced inspiration of fresh intake gases through said intake conduit.

3. An apparatus for administration of a gas to a human and the exhausting thereof comprising in combination:
  (a) a gas flow control including a fixed body member,
  (b) said body member having an intake conduit portion terminating in,
  (c) a single exhaust conduit separate from said intake conduit formed in said body and joining said intake conduit in a V-formation,
  (d) a central conduit formed in said body and intersecting said intake and exhaust conduits at the apex of the V-formation of said intake conduit and said single exhaust conduit,
  (e) mask means having an enclosed hollow body for covering the nose including,
  (f) said mask body including accurate spaced front and rear walls joined by,
  (g) sidewalls and,
  (h) a top end member having an opening connected with said gas flow control body member for communication with said central conduit,
  (i) said front wall terminating in a lower bottom wall,
  (j) said rear wall terminating in an upper bottom wall and having a pair of openings therein communicating with the interior of the hollow mask body, each opening having a protrusion formed therewith for sealing engagement with the nostrils of a human nose,
  (k) said exhaust conduit having manually operable means located therein for occluding the flow of fresh intake gases therethrough whereby the flow of fresh intake gases through said intake conduit are blocked from entering said exhaust conduit and directed to enter said central conduit at said V-formation to allow forced inspiration of fresh intake gases through said intake conduit.

4. A device for administering gas for use in combinations with a gas flow control comprising:
  (a) mask means having an enclosed hollow body for covering the nose including,
  (b) said body including accurate spaced front and rear walls joined, by,
  (c) sidewalls and,
  (d) a top end member having an opening connected with said gas flow control body member for communication with said central conduit,
  (e) said front wall terminating in a lower bottom wall,
  (f) said rear wall terminating in an upper bottom wall, and having a pair of openings therein communicating with the interior of the hollow mask body, each opening having a protrusion formed therewith for sealing engagement with the nostrils of a human nose.

* * * * *

UNITED STATES PATENT OFFICE
CERTIFICATE OF CORRECTION

Patent No. 4,151,843           Dated   May 1, 1979

Inventor(s)   John H. Brekke and Devin R. Lackie

It is certified that error appears in the above-identified patent and that said Letters Patent are hereby corrected as shown below:

The address of inventor John H. Brekke should be

4921 Pike Lane
        Route #1
        Duluth, Mn. 55811

Signed and Sealed this

*Twelfth* Day of *August 1980*

[SEAL]

*Attest:*

SIDNEY A. DIAMOND

*Attesting Officer*      *Commissioner of Patents and Trademarks*

UNITED STATES PATENT AND TRADEMARK OFFICE
CERTIFICATE OF CORRECTION

PATENT NO. : 4,151,843
DATED : May 1, 1979
INVENTOR(S) : John H. Brekke et al.

It is certified that error appears in the above—identified patent and that said Letters Patent is hereby corrected as shown below:

The correct spelling of the name of the second inventor should read:
-- Devin R. Lackie --.

Signed and Sealed this

Sixteenth Day of September 1980

[SEAL]

Attest:

Attesting Officer

SIDNEY A. DIAMOND
Commissioner of Patents and Trademarks